US006982355B2

(12) United States Patent
Abazajian

(10) Patent No.: US 6,982,355 B2
(45) Date of Patent: Jan. 3, 2006

(54) INTEGRATED FISCHER-TROPSCH PROCESS FOR PRODUCTION OF LINEAR AND BRANCHED ALCOHOLS AND OLEFINS

(75) Inventor: Armen N. Abazajian, Houston, TX (US)

(73) Assignee: Syntroleum Corporation, Tulsa, OK (US)

(*) Notice: Subject to any disclaimer, the term of this patent is extended or adjusted under 35 U.S.C. 154(b) by 0 days.

(21) Appl. No.: 10/924,378

(22) Filed: Aug. 23, 2004

(65) Prior Publication Data

US 2005/0085558 A1 Apr. 21, 2005

Related U.S. Application Data

(60) Provisional application No. 60/497,539, filed on Aug. 25, 2003.

(51) Int. Cl.
C07C 45/00 (2006.01)
C07C 29/00 (2006.01)
C07C 27/00 (2006.01)

(52) U.S. Cl. ............... 568/454; 518/700; 568/451; 568/455; 568/850

(58) Field of Classification Search ............... 518/700; 568/454, 455, 850, 451
See application file for complete search history.

(56) References Cited

U.S. PATENT DOCUMENTS

| | | | |
|---|---|---|---|
| 3,852,207 A | 12/1974 | Stangeland et al. |
| 3,871,838 A | 3/1975 | Henkel et al. |
| 3,904,513 A | 9/1975 | Fischer et al. |
| 4,080,397 A | 3/1978 | Derr et al. |
| 4,131,568 A | 12/1978 | Bartish |
| 4,136,015 A | 1/1979 | Kamm et al. |
| 4,147,730 A | 4/1979 | Love et al. |
| 4,157,294 A | 6/1979 | Iwao et al. |
| 4,166,834 A | 9/1979 | Reed et al. |
| 4,207,424 A | 6/1980 | Winnick |
| 4,252,736 A | 2/1981 | Haag et al. |
| 4,306,084 A | 12/1981 | Pettit |
| 4,370,258 A | 1/1983 | Ogata et al. |
| 4,423,274 A | 12/1983 | Daviduk et al. |
| 4,451,679 A | 5/1984 | Knifton et al. |
| 4,451,680 A | 5/1984 | Knifton |
| 4,469,895 A | 9/1984 | Knifton et al. |
| 4,496,768 A | 1/1985 | Dennis et al. |
| 4,496,769 A | 1/1985 | Dennis et al. |
| 4,497,968 A | 2/1985 | Wright et al. |
| 4,506,101 A | 3/1985 | Chang |
| 4,511,740 A | 4/1985 | Alexander et al. |
| 4,513,160 A | 4/1985 | Avidan et al. |
| 4,513,161 A | 4/1985 | Mauldin |
| 4,542,122 A | 9/1985 | Payne et al. |
| 4,547,601 A | 10/1985 | Holland et al. |
| 4,556,752 A | 12/1985 | Mauldin et al. |
| 4,567,306 A | 1/1986 | Dennis et al. |
| 4,568,663 A | 2/1986 | Mauldin |
| 4,579,995 A | 4/1986 | Mauldin |
| 4,582,630 A | 4/1986 | Quang et al. |
| 4,590,314 A | 5/1986 | Kinkade |
| 4,595,703 A | 6/1986 | Payne et al. |
| 4,628,135 A | 12/1986 | Owen et al. |
| 4,640,764 A | 2/1987 | Hamilton, Jr. |
| 4,663,305 A | 5/1987 | Mauldin et al. |
| 4,670,475 A | 6/1987 | Mauldin |
| 4,751,345 A | 6/1988 | Mauldin |
| 4,755,536 A | 7/1988 | Mauldin et al. |
| 4,762,959 A | 8/1988 | Mauldin et al. |
| 4,795,730 A | 1/1989 | Drake |
| 4,832,819 A | 5/1989 | Hamner |
| 4,833,170 A | 5/1989 | Agee |
| 4,973,453 A | 11/1990 | Agee |
| 5,023,389 A | 6/1991 | Grandvallet et al. |
| 5,041,685 A | 8/1991 | Alvila et al. |
| 5,057,637 A | 10/1991 | Sweeney et al. |
| 5,112,527 A | 5/1992 | Kobylinski |
| 5,227,563 A | 7/1993 | Fukuhara et al. |
| 5,475,183 A | 12/1995 | Araki et al. |
| 5,481,044 A | 1/1996 | Weber et al. |
| 5,632,787 A | 5/1997 | Boucot et al. |
| 5,675,041 A | 10/1997 | Kiss et al. |
| 5,723,680 A * | 3/1998 | Kormann et al. ............ 568/455 |
| 5,733,941 A | 3/1998 | Waycuilis |
| 5,811,620 A | 9/1998 | Knifton et al. |
| 5,817,906 A | 10/1998 | Marker et al. |
| 5,861,441 A | 1/1999 | Waycuilis |
| 5,869,434 A | 2/1999 | Mueller et al. |
| 6,085,512 A | 7/2000 | Agee et al. |
| 6,121,504 A | 9/2000 | Kuechler et al. |
| 6,130,259 A | 10/2000 | Waycuilis |
| 6,155,039 A | 12/2000 | Agee et al. |

(Continued)

FOREIGN PATENT DOCUMENTS

EP 0 583 836 3/1994

(Continued)

OTHER PUBLICATIONS

S.A. Ali, H.S. Mazhar et al. "Catalyst Conversion of Isopropanol on A1203-Nd203 Supported on Silica", Afinidad 53 (1996) 61.

(Continued)

Primary Examiner—J. Parsa
(74) Attorney, Agent, or Firm—Baker & McKenzie LLP; Valerie K. Friedrich

(57) ABSTRACT

A process is disclosed for making high value olefins and alcohols from synthesis gas as well as a process for an improved yield of alpha-olefins from synthesis gas. The process for hydroformulation of olefins is also provided.

12 Claims, No Drawings

U.S. PATENT DOCUMENTS

| | | |
|---|---|---|
| 6,169,120 B1 | 1/2001 | Beer |
| 6,172,124 B1 | 1/2001 | Wolflick et al. |
| 6,184,424 B1 | 2/2001 | Bueschken et al. |
| 6,225,507 B1 | 5/2001 | Giessler et al. |
| 6,310,261 B1 | 10/2001 | Geissler et al. |
| 6,331,657 B1 | 12/2001 | Kaizik et al. |
| 6,344,491 B1 | 2/2002 | Beer et al. |
| 6,365,783 B1 | 4/2002 | Yokomori et al. |
| 6,384,170 B1 | 5/2002 | Krull et al. |
| 6,447,745 B1 | 9/2002 | Feeley et al. |
| 6,482,992 B2 | 11/2002 | Scholz et al. |
| 6,486,362 B1 | 11/2002 | Forestiere et al. |
| 6,497,812 B1 | 12/2002 | Schinski |
| 6,500,991 B2 | 12/2002 | Wiese et al. |
| 6,518,473 B2 | 2/2003 | Miller et al. |
| 2001/0021724 A1 | 9/2001 | Arcuri et al. |
| 2002/0003102 A1 | 1/2002 | O'Rear et al. |
| 2002/0019574 A1 | 2/2002 | Ueda et al. |
| 2002/0028974 A1 | 3/2002 | Scholtz et al. |
| 2002/0147376 A1 | 10/2002 | Fung et al. |
| 2003/0010677 A1 | 1/2003 | Schinski |
| 2003/0040652 A1 | 2/2003 | Ansorge et al. |
| 2004/0167234 A1 | 8/2004 | Abazajian |

FOREIGN PATENT DOCUMENTS

| | | |
|---|---|---|
| EP | 1 101 813 | 5/2001 |
| WO | WO 01/46096 | 6/2001 |
| WO | WO 03/066777 | 8/2003 |

OTHER PUBLICATIONS

Jose Corella and Jose M. Asua, "Kinetics and Mechanism of Deactivation by Fouling of a Silica-Alumina Catalyst", The Canadian Journ. of Chem. Eng., vol. 59, Aug. 1981, pp. 506-510.

R.M. Cursetji, A.N. Singh and A.C. Deo, "Ethylene from Ethyl Alcohol on High Silica Zeolite Catalyst", Chem. Age of India, vol. 37, No. 6, Jun. 1986, pp. 407-410.

Natarajan, G.S. et al. "Alumina Catalyst for Alcohol Dehydration", Indian Journal of Tech., 10 (1972): pp. 463-464.

U.S. Appl. No 10/682,244, filed Oct. 9, 2003, Abazajian et al.

PCT Search Report for Application No. PCT/US04/27515 dated May 17, 2005.

* cited by examiner

INTEGRATED FISCHER-TROPSCH PROCESS FOR PRODUCTION OF LINEAR AND BRANCHED ALCOHOLS AND OLEFINS

CROSS REFERENCE TO RELATED APPLICATIONS

This application claims priority to Provisional Application Ser. No. 60/497,539, filed on Aug. 25, 2003.

FEDERALLY SPONSORED RESEARCH

Not applicable.

REFERENCE TO MICROFICHE APPENDIX

Not applicable.

FIELD OF THE INVENTION

The process of the invention relates generally to production of linear and branched alcohols and olefins.

BACKGROUND OF THE INVENTION

Currently two methods of making high-value products via Fischer-Tropsch synthesis are predominately utilized. The first, a high temperature Fischer-Tropsch synthesis, makes a high fraction of olefins in the product, but also makes a large variety of olefin, paraffin, naphthene, aromatic, alcohol, aldehyde, carboxylic acid and carboxylic ester isomers. The separation of all these isomers is extremely difficult and involves a number of steps, including, but not limited to, isomeric distillation, solvent extraction, and extractive distillation. The second process, a low temperature Fischer-Tropsch synthesis produces primarily normal paraffins solvents, naphthas, and waxes. A number of processes to hydrocrack and hydroisomerize Fischer-Tropsch waxes into a variety of isoparaffin products such as isoparaffin solvents, naphthas, and lubricant basestocks are known n the art. However, many of the high-volume, high-value olefin and alcohol applications require high linearity or specific branching of the olefin and/or alcohol products. Such highly linear or specifically branched olefins and alcohols are very difficult to separate from high-temperature Fischer-Tropsch products. Moreover, no viable processes for isolating such alcohols and olefins from low-temperature Fischer-Tropsch products are known.

One characteristic of one low temperature Fischer-Tropsch process is the high degree of linearity of the product hydrocarbons. Moreover, where the product is not entirely linear, the branching is predominately specifically monomethyl and terminal. As used herein, the term "terminal" indicates a location at the second or third carbon from the end of the chain. Such low temperature Fischer-Tropsch process is described in the commonly-owned co-pending U.S. application Ser. Nos. 10/426,154, which is incorporated herein by reference. Depending on the carbon number, between about 30% to about 90% of the product may be composed of normal paraffins, and less than about 15%, but most likely less than about 5% of each carbon number component may be the methyl-branched iso-paraffins.

The olefin content of the low temperature Fischer-Tropsch synthesis product may range from as high as 50% at $C_4$ with as much as about 40% being alpha-olefins and about 10% being internal olefins. Conversely, at $C_{14}$, the total olefins may be 10% or less, with less than 5% internal olefins. In addition to normal paraffins, isoparaffins, and olefins, such low temperature Fischer-Tropsch process generally produces from between about 5 to about 15% oxygenates, depending on the carbon number. The oxygenates are predominantly primary alcohols.

SUMMARY OF THE INVENTION

In one embodiment of the invention, an integrated process to make linear and specifically-branched alcohols and olefins from synthesis gas derived from gas or coal feedstocks is provided. The process incorporates dehydration of all or part of a Fischer-Tropsch synthesis product to produce a mixture of olefins and paraffins. The resulting olefin/paraffin mixture is separated into olefins and paraffins. The olefins may optionally be isomerically distilled to make high-value alpha-olefins. The paraffins may be dehydrogenated to mono-olefins, combined with the internal olefins rejected by distillation and hydroformulated to high-value alcohols. Primary alcohols in the Fischer-Tropsch synthesis product may be distilled into specific cuts isomerically and then dehydrated to form linear alpha-olefins in very high yield thus increasing the overall yield of alpha-olefins from low temperature Fischer-Tropsch synthesis.

BRIEF DESCRIPTION OF THE DRAWINGS

None.

DESCRIPTION OF EMBODIMENTS OF THE INVENTION

Embodiments of the integrated Fischer-Tropsch process of the invention include processing of synthesis gas to produce a hydrocarbon stream via the Fischer-Tropsch reaction, recovery of the Fischer-Tropsch product, catalytic dehydration of all or part of the Fischer-Tropsch product, and recovery of the hydrocarbons by phase separation. Optional steps incorporated in some embodiments of the integrated process include production of a synthesis gas, fractionation or distillation of the Fischer-Tropsch product prior to dehydration and hydroprocessing of part of the Fischer-Tropsch hydrocarbon product. A wide variety of Fischer-Tropsch reaction processes are known in which reaction conditions, catalysts, and reactor configurations vary. The integrated Fischer-Tropsch process of the invention may be used with any such reaction conditions, catalysts, and reactor configurations. For the purposes of the description below, one known Fischer-Tropsch synthesis is described. Other variations of Fischer-Tropsch synthesis are described, inter alia, in U.S. Pat. Nos. 4,973,453; 6,172,124; 6,169,120; and 6,130,259; the disclosures of which are all incorporated herein by reference.

Three basic techniques may be employed for producing a synthesis gas, or syngas, which is used as the starting material of a Fischer-Tropsch reaction. These include oxidation, reforming and autothermal reforming. As an example, a Fischer-Tropsch conversion system for converting hydrocarbon gases to liquid or solid hydrocarbon products using autothermal reforming includes a synthesis gas unit, which includes a synthesis gas reactor in the form of an autothermal reforming reactor ("ATR") containing a reforming catalyst, such as a nickel-containing catalyst. A stream of light hydrocarbons to be converted, which may include natural gas, is introduced into an ATR along with an oxygen-containing gas which may be compressed air, other compressed oxygen-containing gas, or pure oxygen. The ATR reaction may be adiabatic, with no heat being added or removed from the reactor other than from the feeds and the heat of reaction. The reaction is carried out under sub-stoichiometric conditions whereby the oxygen/steam/gas mixture is converted to syngas.

The Fischer-Tropsch reaction for converting syngas, which is composed primarily of carbon monoxide (CO) and hydrogen gas ($H_2$), may be characterized by the following general reaction:

$$2nH_2 + nCO \rightarrow (\text{---}CH_2\text{---})_n + nH_2O \quad (1)$$

Non-reactive components, such as nitrogen, may also be included or mixed with the syngas. This may occur in those instances where air, enriched air, or some other non-pure oxygen source is used during the syngas formation.

The syngas is delivered to a synthesis unit, which includes a Fischer-Tropsch reactor (FTR) containing a Fischer-Tropsch catalyst. Numerous Fischer-Tropsch catalysts may be used in carrying out the reaction. These include cobalt, iron, ruthenium as well as other Group VIIIB transition metals or combinations of such metals, to prepare both saturated and unsaturated hydrocarbons. The Fischer-Tropsch catalyst may include a support, such as a metal-oxide support, including silica, alumina, silica-alumina or titanium oxides. For example, a Co catalyst on transition alumina with a surface area of approximately 100–200 $m_2/g$ may be used in the form of spheres of 50–150 $\mu m$ in diameter. The Co concentration on the support may also be 15–30%. Certain catalyst promoters and stabilizers may be used. The stabilizers include Group IIA or Group IIIB metals, while the promoters may include elements from Group VIII or Group VIIB. The Fischer-Tropsch catalyst and reaction conditions may be selected to be optimal for desired reaction products, such as for hydrocarbons of certain chain lengths or number of carbon atoms. Any of the following reactor configurations may be employed for Fischer-Tropsch synthesis: fixed bed, slurry bed reactor, ebullating bed, fluidizing bed, or continuously stirred tank reactor (CSTR). The FTR may be operated at a pressure of 100 to 500 psia and a temperature of 375° F. to 500° F. The reactor gas hourly space velocity ("GHSV") may be from 1000 to 8000 $hr^{-1}$. Syngas useful in producing a Fischer-Tropsch product useful in the invention may contain gaseous hydrocarbons, hydrogen, carbon monoxide and nitrogen with $H_2/CO$ ratios from about 1.8 to about 2.4. The hydrocarbon products derived from the Fischer-Tropsch reaction may range from methane ($CH_4$) to high molecular weight paraffinic waxes containing more than 100 carbon atoms.

Referring to FIG. 1, an overview of the integrated Fischer Tropsch process is illustrated. Synthesis gas contained in line 1 is fed to a Fischer-Tropsch reactor (FTR) 2. The tail gas of the Fischer-Tropsch product is recovered overhead in line 3 and the Fischer-Tropsch oil and wax are fractionated and recovered through lines 4 and 5. The product recovered in line 4 is a Light Fischer Tropsch Liquid (LFTL), and the product recovered in line 5 is a Heavy Fischer Tropsch Liquid (HFTL). Alternatively, LFTL and HFTL may be further fractionated into at least a nominally 30–550° F. distillate and 500° F.+ bottoms stream. LFTL and HFTL may also be fractionated into a number of other fractions as required by the desired product slate.

The HFTL stream can be hydroprocessed into a number of fuel or lubricant products as described in the processes disclosed in Appendix A. The hydrocracker naphtha overheads may be dehydrogenated to form branched mono-olefins.

All or part of the LFTL fraction is vaporized and dehydrated in a dehydration reactor over alumina, preferably passivated alumina, such that the majority of the alpha-olefins present in the LFTL before dehydration as well as those formed by dehydration are retained. During the dehydration reaction the alcohols react to yield corresponding olefins according to the following reaction:

$$R\text{---}CH_2\text{---}CH_2\text{---}OH \rightarrow R\text{---}CH\text{=}CH_2 + H_2O \quad (2)$$

The reaction is conducted from about 500° F. to about 700° F. and at pressures sufficiently low to maintain the stream fully vaporized. The conversion of alcohols to olefins is between 95% and about 100%. The dehydrated LFTL is then condensed and the phases are separated. The dehydration step enriches the olefin content of the stream by converting the alcohols into corresponding olefins.

Following phase separation, the non-aqueous phase may be fractionated into a number of fractions, including for example, $C_9$- and $C_{10}$–$C_{13}$ cuts. The fractions and boiling point/carbon number cutoffs generally depend upon the desired product slate.

Alpha and internal-olefins in the dehydrated LFTL stream may then be hydroformulated in a process commonly known as the "OXO" process, illustrated by equation (3). The OXO process to make alcohols is described in detail in Kirk-Othmer Encyclopedia of Chemical Technology, 4th Edition, Volume 1, pp. 903–8 (1991).

$$R\text{---}CH\text{=}CH + CO/H_2 \rightarrow R\text{---}CH_2\text{---}CH_2\text{---}CH\text{=}O \quad (3)$$

The hydroformulation product is hydrogenated to form alcohols either in the step illustrated in equation (3), or in a second step, illustrated by equation (4) below:

$$R\text{---}CH_2\text{---}CH_2\text{---}CH\text{=}O + H_2 \rightarrow R\text{---}CH_2\text{---}CH_2\text{---}CH\text{---}OH \quad (4)$$

The OXO process is characterized mainly by a certain ratio of normal product to isomeric product and the pressure of the reaction. A conventional OXO process employs a Co-hydrocarbonyl catalyst at pressures from about 3000 psig to about 5000 psig, temperatures from about 110° to about 180° C., and a ratio of $CO:H_2$ of about 1:1. The OXO process is a two-step process, wherein first the aldehyde is formed and separated, and second the aldehyde is hydrogenated to alcohols or oxidized to acids.

A process employed by Shell functions at around 400 psig and uses a cobalt catalyst liganded with a tributyl phosphine instead of one of the carbonyl ligands. It requires a ratio of $CO:H_2$ of 1:2 and generates an alcohol product in a single step.

A commercially available process, licensed by Davy Process Technology, uses an Rh catalyst with a triphenyl phosphine ligand in a two-stage low-pressure process (~300 psig) with 1:1 $CO:H_2$. Both the Davy Process Technology and Shell processes produce products with high linearity, the ratio of linear product to branched product being at least about 10:1.

Another useful feature of the OXO process is that it converts alpha-olefins much more readily than internal olefins and occurs in an isomerizing atmosphere. Thus, even internal olefins are partially converted into linear alcohols. The Shell process converts 75% of feed internal olefins to primary alcohols, while Davy process reportedly converts even more. Although normally a synthesis gas without diluents is used, a synthesis gas from the Syntroleum ATR containing from about 10 to about 60% $N_2$ may be utilized. Because hydroformulation adds a ---COH group to an olefin, the lightest of the produced alcohols will boil higher than the heaviest of the contained olefins, thus making the separation relatively facile.

Following the OXO reaction, and distillation of alcohols away from paraffins, the alcohol blends are in marketable cuts. Such cuts include, for example, $C_6$–$C_{10}$ alcohols, useful as plasticizers and $C_{11}$–$C_{14}$ alcohols, useful as surfactant feedstocks.

The paraffins separated from the alcohols can be catalytically dehydrogenated predominantly to internal mono-olefins and fed to hydroformulation for conversion of the internal olefins to predominantly linear alcohols. Dehydrogenation of linear paraffins to mono-olefins is well known, at least for the $C_2$–$C_5$ range and $C_{10}$–$C_{14}$ range. A well known dehydrogenation process is the UOP Pacol™ process. Syntroleum has demonstrated the feasibility of dehydrogenation of $C_6$–$C_9$ paraffins to mono-olefins.

In yet another embodiment, $C_6$, $C_8$ and $C_{10}$ OXO primary alcohols have valuable olefin counterparts. Such primary alcohols may be distilled into single cuts and purified in isomeric distillation. The branched isomers are combined with the plasticizer cut. The primary alcohols can be dehydrated in a process already described above and high purity alpha-olefins can be made. The advantage of this production route, using intermediate alcohol cuts, is that the yield of alpha-olefins per carbon number is greatly increased, especially for these lighter numbers. For example, yields of $C_6$ and $C_8$ alpha-olefin can be increased by as much as a factor of 3 or 4 by converting most of internal olefins to linear primary alcohols, which then can be dehydrated to alpha-olefins.

In an alternative embodiment, the dehydrated LFTL stream, after phase separation, may be processed through a molecular sieve to separate olefins from paraffins (for example, UOP's OLEX™ process). The olefins can then be distilled into separate useful cuts. $C_6$, $C_8$ and $C_{10}$ olefins can be distilled as single cuts, and then subjected to isomeric distillation to remove internal olefins. High value applications for $C_6$ and $C_8$ alpha-olefins are as polyethylene comonomers. $C_{10}$ alpha-olefin is a feedstock for polyalphaolefins production, a synthetic lubricant basestock. $C_{10}$–$C_{13}$ linear and internal olefins find ready application as linear alkylbenzene and synthetic alcohol feedstocks. $C_{14}$ to $C_{18}$ linear and internal olefins are used as drilling fluids feedstocks, lubricant additive intermediates and alkyl succinic anhydride feedstocks. The paraffins separated in the molecular sieve are fed to dehydrogenation as described above and recycled to molecular sieve in a campaign mode to separate internal olefins from paraffins. Since relatively few alpha olefins are made in dehydrogenation, this feedstock should not be mingled with the dehydrated feedstock to preserve high concentration of alpha-olefins in the dehydrated feedstock.

What is claimed is:

1. An integrated process to make high value linear alcohols, branched alcohols and linear olefins from synthesis gas wherein:
    a) separating a Fischer-Tropsch synthesis product into HFTL and LFTL fractions;
    b) contacting the LFTL fraction with a dehydration catalyst to produce a dehydrated LFTL fraction comprising olefins and paraffins;
    c) separating the dehydrated LFTL fraction into at least $C_5$–$C_9$ and $C_{10}$–$C_{13}$ olefin/paraffin fractions; and
    d) contacting the $C_5$–$C_9$ and $C_{10}$–$C_{13}$ olefin/paraffin fractions with synthesis gas to form $C_5$–$C_9$ and $C_{10}$–$C_{13}$ aldehyde/paraffin fractions.

2. The process of claim 1 further comprising the step of:
    e) reacting the aldehydes in the $C_5$–$C_9$ and $C_{10}$–$C_{13}$ aldehyde/paraffin fractions with hydrogen gas to form $C_5$–$C_9$ and $C_{10}$–$C_{13}$ alcohol/paraffin fractions.

3. The process of claim 2 further comprising the step of:
    f) distilling the $C_5$–$C_9$ and $C_{10}$–$C_{13}$ alcohol/paraffin fractions to obtain $C_5$–$C_9$ and $C_{10}$–$C_{13}$ alcohol fractions and $C_5$–$C_9$ and $C_{10}$–$C_{13}$ paraffin fractions.

4. The process of claim 3 further comprising the steps of:
    g) combining and dehydrogenating the $C_5$–$C_9$ and $C_{10}$–$C_{13}$ paraffin fractions to form a $C_5$–$C_{13}$ fraction comprising olefins; and
    h) recycling the $C_5$–$C_{13}$ fraction comprising olefins to step d).

5. The process of claim 3 further comprising the step of:
    i) distilling the $C_5$–$C_9$ and $C_{10}$–$C_{13}$ alcohol fractions to obtain individual carbon number alcohol fractions.

6. The process of claim 5 further comprising the step of:
    j) isomerically distilling one or more individual carbon number alcohol fractions to obtain one or more fractions of individual carbon number linear alcohol fractions.

7. The process of claim 6 further comprising the step of:
    k) dehydrating one or more fractions of individual carbon number linear alcohol fractions to form one or more corresponding high-linearity alpha-olefin fractions.

8. The process of claim 1 further comprising the steps of:
    m) hydroprocessing the HFTL to produce a $C_5$–$C_9$ branched naphtha fraction; and
    n) dehydrogenating the $C_5$–$C_9$ branched naphtha to form a $C_5$–$C_9$ internal olefin fraction.

9. The process of claim 8 further comprising the step of:
    o) hydroformylating the $C_5$–$C_9$ internal olefin fraction comprising the steps of:
        i) reacting the $C_5$–$C_9$ internal olefins with synthesis gas to form a $C_5$–$C_9$ branched aldehyde/paraffin fraction; and
        ii) reacting the $C_5$–$C_9$ branched aldehyde/paraffin fraction with hydrogen gas to form a $C_5$–$C_9$ branched alcohouparaffin fraction.

10. The process of claim 1 wherein the dehydrated LFTL is passed over a molecular sieve and $C_6$ and $C_8$ olefin fractions are separated.

11. The process of claim 10 further comprising the step of isomerically distilling the $C_6$ and $C_8$ olefin fractions to obtain $C_6$ and $C_8$ alpha-olefin fractions.

12. An integrated process to make high value linear alcohols, branched alcohols and linear olefins from synthesis gas wherein:
    a) separating a Fischer-Tropsch synthesis product into HFTL and LFTL fractions;
    b) contacting the LFTL fraction with a dehydration catalyst to produce a dehydrated LFTL fraction comprising olefins and paraffins;
    c) separating the dehydrated LFTL fraction into at least $C_5$–$C_9$ and $C_{10}$–$C_{13}$ olefin/paraffin fractions; and
    d) contacting the $C_5$–$C_9$ and $C_{10}$–$C_{13}$ olefin/paraffin fractions with synthesis gas to form $C_5$–$C_9$ and $C_{10}$–$C_{13}$ aldehyde/paraffin/alcohol fractions.

* * * * *

UNITED STATES PATENT AND TRADEMARK OFFICE
CERTIFICATE OF CORRECTION

PATENT NO. : 6,982,355 B2
APPLICATION NO. : 10/924378
DATED : January 3, 2006
INVENTOR(S) : Armen Abazajian It is certified that error appears in the above-identified patent and that said Letters Patent is hereby corrected as shown below:

Column 6,
Line 42, replace "alcohoupariffin" with -- alcohol/paraffin --.

Signed and Sealed this

Twentieth Day of June, 2006

JON W. DUDAS
*Director of the United States Patent and Trademark Office*